US007859674B2

(12) United States Patent
Greten et al.

(10) Patent No.: US 7,859,674 B2
(45) Date of Patent: Dec. 28, 2010

(54) SYSTEM AND METHOD FOR MEASURING A HARVEST QUALITY PARAMETER ON A HARVESTING DEVICE (75) Inventors: Wilhelm G. Greten, Saerbeck (DE); Carlos Hildebrand, Münstertal (DE); Roland Welle, Steinenstadt (DE)

(73) Assignee: Pioneer Hi-Bred International, Inc., Johnston, IA (US)

( * ) Notice: Subject to any disclaimer, the term of this patent is extended or adjusted under 35 U.S.C. 154(b) by 502 days.

(21) Appl. No.: 11/942,293

(22) Filed: Nov. 19, 2007

(65) Prior Publication Data
US 2008/0137087 A1 Jun. 12, 2008

Related U.S. Application Data (60) Provisional application No. 60/866,476, filed on Nov. 20, 2006.

(51) Int. Cl.
*G01N 21/55* (2006.01)
(52) U.S. Cl. .................... 356/445; 356/443; 356/448; 702/51; 702/41; 702/81; 702/22
(58) Field of Classification Search ............ 356/443, 356/408, 445, 448; 702/81, 54, 1.13, 74, 702/5, 41, 22
See application file for complete search history.

(56) References Cited

U.S. PATENT DOCUMENTS

| | | | |
|---|---|---|---|
| 4,896,795 A * | 1/1990 | Ediger et al. ............ 324/664 |
| 5,751,421 A | 5/1998 | Wright et al. | |
| 5,982,501 A | 11/1999 | Benz et al. | |
| 5,991,025 A | 11/1999 | Wright et al. | |
| 6,421,990 B1 | 7/2002 | Ohlemeyer et al. | |
| 6,483,583 B1 | 11/2002 | Wright et al. | |
| 6,845,326 B1 * | 1/2005 | Panigrahi et al. .............. 702/49 |
| 7,265,831 B2 * | 9/2007 | Kormann et al. ............ 356/328 |

(Continued)

FOREIGN PATENT DOCUMENTS

EP   0 511 184 A1   10/1992

(Continued)

OTHER PUBLICATIONS

The International Search Report and Written Opinion for International Appl. No. PCT/US2007/085069, mailed May 21, 2008.

*Primary Examiner*—Gregory J Toatley
*Assistant Examiner*—Iyabo S Alli
(74) *Attorney, Agent, or Firm*—Alston & Bird LLP (57) ABSTRACT

A system and method for measuring a quality parameter of a harvested crop are provided. Specifically, the system is adapted to be carried by a harvesting device such that a sensor is enclosed in a controlled environment and such that the sensor is capable of precisely and reliably measuring the quality parameter while the harvesting device is in operation. The system includes a verification device and an actuator device contained within the controlled environment. The actuator device periodically conveys the sensor device to at least one of a verification position relative to the verification device and a measurement position. Thus, the sensor device may be periodically and reliably referenced and/or validated while in use in harsh agricultural environments such that the sensor device is capable of accurately measuring the quality parameter as the crop is harvested.

42 Claims, 7 Drawing Sheets

U.S. PATENT DOCUMENTS

2005/0195406 A1 9/2005 Kormann et al.
2006/0027750 A1 2/2006 Kormann et al.
2006/0093522 A1 5/2006 Kormann et al.

FOREIGN PATENT DOCUMENTS

| EP | 1 577 663 A1 | 9/2005 |
| EP | 1 570 723 A1 | 10/2007 |
| WO | WO 99/40419 A1 | 8/1999 |

* cited by examiner

FIG. 6A

SYSTEM AND METHOD FOR MEASURING A HARVEST QUALITY PARAMETER ON A HARVESTING DEVICE

CROSS-REFERENCE TO RELATED APPLICATIONS

This application claims priority from U.S. Provisional Application No. 60/866,476, filed Nov. 20, 2006, which is hereby incorporated herein in its entirety by reference.

FIELD OF THE INVENTION

The various embodiments of the present invention are directed to a system for substantially automating the quality control of a measuring device carried by a harvesting device for measuring quality parameters in a harvested crop.

BACKGROUND OF THE INVENTION

Farmers and agricultural researchers often measure quality parameters such as, for example, moisture, digestibility, starch content, oil content, sugar content, protein content, and/or neutral detergent fiber (NDF) content. Such quality parameters may be measured using sensor devices mounted on a harvesting device (such as a chopper or combine, for example).

Sensor devices (such as near-infrared reflection (NIR) devices, for example) used to measure harvest quality parameters are often exposed to the elements (such as rain, dust, and light). Because the output of such sensor devices may be affected by slight changes in environmental parameters (such as light, temperature, and humidity, for example), sensor devices carried in conventional sensor device mounts on harvesting devices often record inaccurate measurements of quality parameters. Moreover, conventional sensor device housings configured to carry such sensor devices do not include mechanisms and/or facilities for allowing checks and/or verification procedures that may allow a user to ensure that the sensor devices are operating to specifications during operation of the harvesting device.

Furthermore, conventional methods for referencing and/or validating the sensor devices may be disruptive to the measurement of the quality parameter and/or may result in substantially inaccurate data. For example, referencing (such as "manual zeroing," for example) and/or validating of sensor devices (such as NIR devices, for example) carried by harvesting devices is typically time consuming and interrupts operations because the harvesting device must be stopped each time the sensor device is referenced and/or validated. Thus, due to time constraints, referencing and/or validation procedures are often not performed often enough to produce optimal harvest quality parameter data.

Some conventional devices for mounting sensor devices on a harvesting device may include chain-driven rotational devices for moving a sensor device about a central axis such that the sensor device may be selectively aligned with one or more verification references (such as, for example, a white, black, and/or colored tile having known reflectance characteristics). However, because the rotation of such conventional devices is sometimes imprecise, the device sometimes fails to optimally position the sensor device (such as an NIR device) relative to the verification reference. For example, in some cases, it is crucial that the sensor device is positioned at the same position relative to a maximum reflectance reference (such as a white reference tile, for example) as each position on a given reference tile may have slight variations in shade (and therefore, in reflectance). In addition, imprecise movement of the sensor device may also result in an erroneous attempt to reference the sensor device outside the boundaries of the reference tile. Thus, such conventional devices may result in the improper and/or incomplete referencing of the sensor device.

Therefore, in order to facilitate the economical, reliable, and accurate measurement of quality parameters, there is a need in the art for a system, device, and method that allows for accurate referencing of a quality parameter sensor device mounted on a harvesting device (such as a chopper or combine, for example). Furthermore, there exists a need for a system, device, and method that allows for control of environmental parameters in the measurement environment. There also exists a need for a system, device, and method that allows for real-time validation of the functionality of the sensor device (using, for example, reference crop samples having known characteristics). There further exists a need for a system, device, and method that allows for precise control of the movement of the sensor device relative to one or more referencing and/or validation standards.

SUMMARY OF THE INVENTION

The various embodiments of the present invention satisfy the needs listed above and provide other technical advantages as described below. Embodiments of the present invention provide a system for measuring a quality parameter of a harvested crop. According to some embodiments, the system may be adapted to be carried by a harvesting device (such as a chopper, for example). According to some embodiments, the system comprises a sensor device configured to be capable of measuring a quality parameter of a harvested crop.

Furthermore, in one embodiment, the system comprises a sensor device enclosure configured to contain the sensor device in a controlled environment defined by at least one environmental parameter. Such system embodiments further comprise a verification device disposed within the sensor device enclosure, wherein the verification device is characterized by a known parameter. The system further comprises an actuator device configured to selectively convey the sensor device to a measuring position relative to the harvesting device such that the sensor device is capable of measuring the quality parameter of the harvested crop. The actuator device is further configured to selectively convey the sensor device to a verification position substantially adjacent to the verification device such that the sensor device is capable of measuring a verification parameter of the verification device. Thus, according to such embodiments, the system may be configured to be capable of verifying the proper operation of the sensor device by comparing the known parameter of the verification device to the verification parameter measured by the sensor device when the sensor device is conveyed to the verification position.

In some system embodiments, the verification device may include, but is not limited to: a reference tile (such as, for example, black or white reference tiles); a validation crop sample (characterized by a known quality parameter, for example, such as a known moisture content corresponding to a known reflectance); and combinations of such verification standards. In some embodiments (wherein the verification device comprises a reference standard, such as a white or black tile, for example), the known parameter may comprise a known reflectance of the reference standard. Furthermore, the known parameter of the verification device (wherein the verification device comprises a validating crop sample, for example) may include, but is not limited to: a moisture of the validation crop sample; a starch content of the validation crop sample; an oil content of the validation crop sample; a sugar content of the validation crop sample; a protein content of the validation crop sample; a digestibility measure of the validation crop sample; a neutral detergent fiber content of the validation crop sample; and combinations of such known validation parameters.

Furthermore, according to various system embodiments, the sensor device enclosure may be configured to contain the sensor device in a controlled environment defined by at least one environmental parameter. For example, the sensor device enclosure may comprise a substantially light-reflective material disposed on an outer surface of the sensor device enclosure to reduce the accumulation of heat within the enclosure. In other embodiments, the sensor device enclosure may further comprise an insulating material such that heat transfer between an interior of the sensor device enclosure and an exterior of the sensor device enclosure is minimized. In yet another system embodiment, the system may comprise an air-conditioning device operably engaged with the sensor device enclosure and in fluid communication with the sensor device enclosure via at vent aperture defined in the sensor device enclosure. The air-conditioning device may be configured to control the at least one environmental parameter. Furthermore, the sensor device enclosure may define a vent aperture configured to be operably engaged with a conduit for conveying an air flow to alter the at least one environmental parameter. According to various system embodiments, the controlled environmental parameter within the sensor device enclosure may include, but is not limited to: temperature; humidity; light levels; dust concentration; and combinations of such environmental parameters.

In some system embodiments, the actuator device may comprise a linear actuator device for conveying the sensor device to at least one of the measuring position and one or more verification positions. According to some such embodiments, the linear actuator device may further comprise a screw drive for conveying the sensor device to at least one of the measuring position and one or more verification positions. Furthermore, in some embodiments, the actuator device may further comprise a plurality of adjustable stops corresponding to a plurality of discrete positions including at least one of the measuring position and one or more verification positions. According to such embodiments, the linear actuator device may be configured to be responsive to the adjustable stops so as to be capable of conveying the sensor device to each of the plurality of discrete positions. In other embodiments, the actuator device may comprise a rotational actuator device for conveying the sensor device to at least one of the measuring position and the verification position. The system may further comprise, a second actuator device configured to selectively convey the verification device relative to the sensor device such that the sensor device is capable of measuring one or more verification parameters of the verification device.

The embodiments of the present invention also provide a method for measuring a quality parameter of a harvested crop. The method comprises steps for enclosing a sensor device in an enclosure configured to contain the sensor device in a controlled environment defined by at least one environmental parameter. The method further comprises conveying the sensor device to a verification position substantially adjacent to a verification device. As described herein, the verification device is disposed within the sensor device enclosure and is characterized by a known parameter. The method also comprises steps for comparing the known parameter of the verification device to a verification parameter measured by the sensor device when the sensor device is conveyed to the verification position and controlling the lower and upper acceptable limits of a detected difference between the known and measured parameter (such as moisture and other constituent contents, for example). Finally, the method further comprises conveying the sensor device to a measuring position relative to the harvesting device such that the sensor device is capable of measuring the quality parameter of the harvested crop.

Thus the various embodiments of the device and method of the present invention provide many advantages that may include, but are not limited to: providing a substantially dust-free, light-protected, air-conditioned, and/or light-conditioned environment for a sensor device carried by a harvesting device such that the sensor device may be capable of reliably measuring a quality parameter of a harvested crop; providing a system for precisely conveying a sensor device to a plurality of verification and measurement positions within a controlled enclosure such that the sensor device may be reliably referenced, validated and/or used to measure a quality parameter of a harvested crop while being carried on board a harvesting device; and providing a system that allows a sensor device to be reliably referenced and/or validated while in use in an agricultural environment.

These advantages, and others that will be evident to those skilled in the art, are provided in the system, method, and computer program product of the present invention.

BRIEF DESCRIPTION OF THE DRAWINGS

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 2:
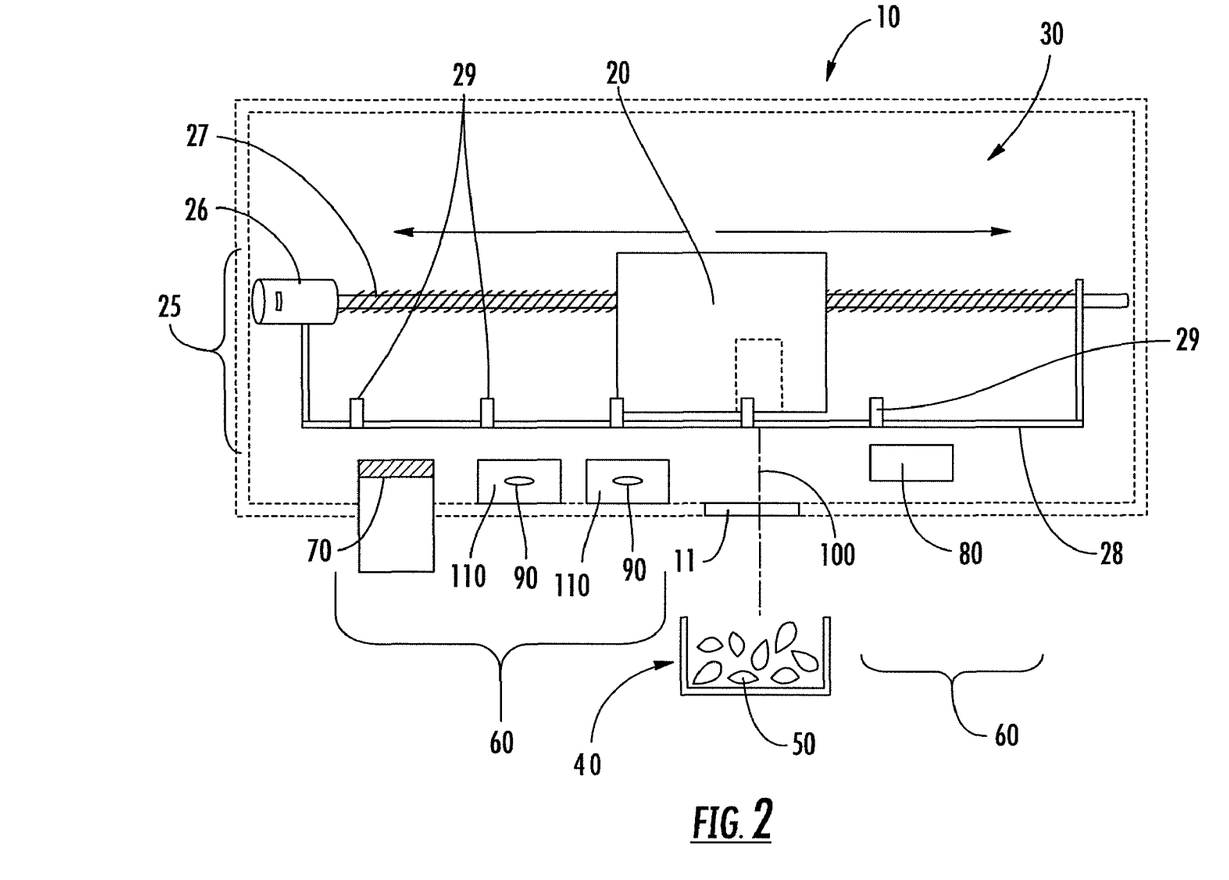
FIG. 2 shows a schematic detailing a sensor device and an actuator device configured to convey the sensor device to various verification and measuring locations, according to one embodiment of the present invention.

It should be understood that the term "verification device" 60 as used herein, may refer generally to devices capable of performing both referencing (which may include "zeroing," for example) functions and validation functions. For example, as described further herein the "verification device" 60 may comprise reference tiles 70, 80 for establishing zero, 100%, and/or other reference reflectance values. Furthermore, the term "verification device," 60 as used herein, may also refer generally to one or more validation check cells 110 (containing validation crop samples 90, for example, as shown in FIG. 2) for validating the operation of the sensor device 20.

Figure 1:
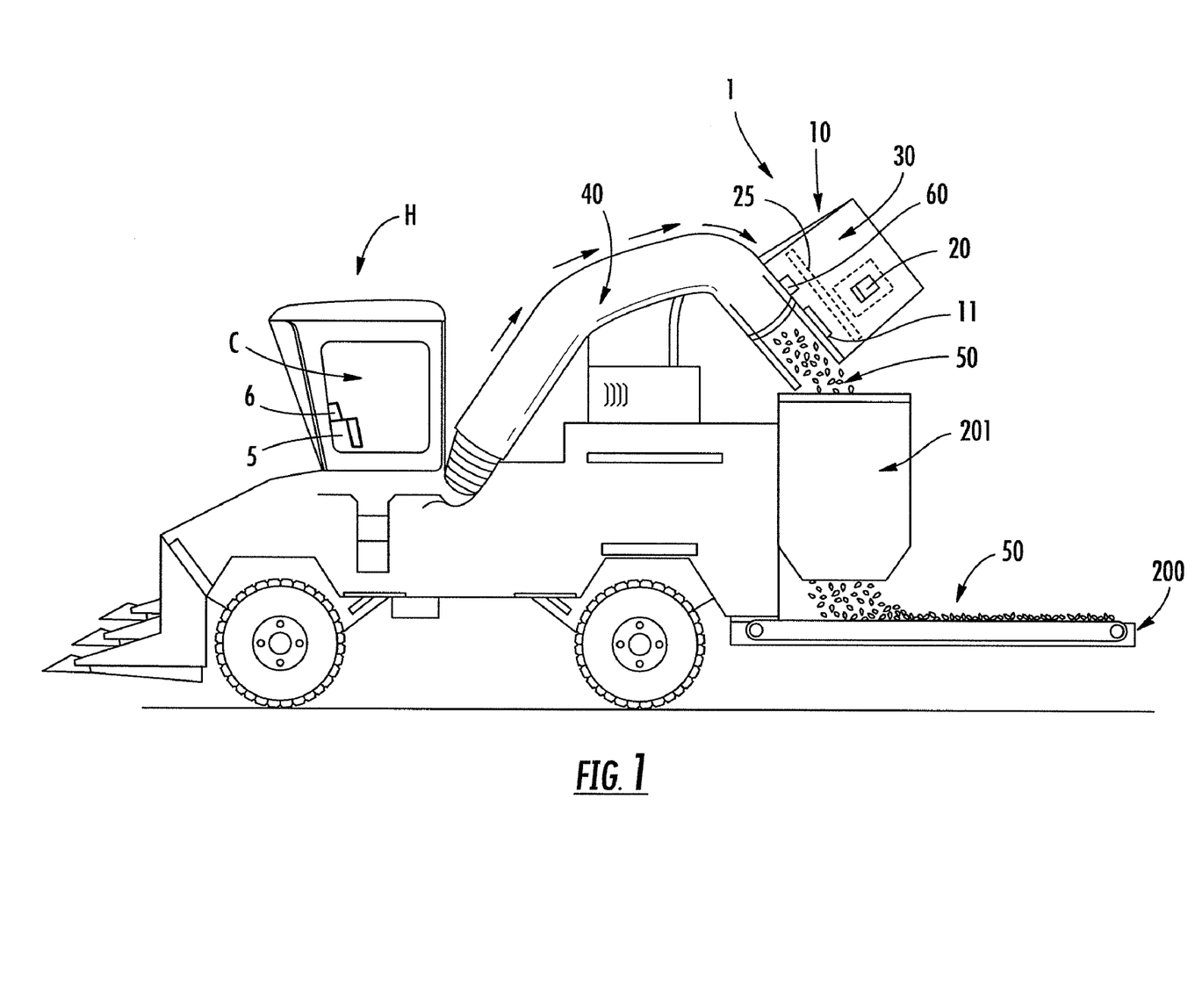
FIG. 1 shows a schematic view of an enclosed system for measuring a parameter of a harvested crop carried by a harvesting device, according to one embodiment of the present invention.

FIG. 1 illustrates an exemplary system 1 for enclosing a sensor device 20 in a sensor device enclosure 10 such that the sensor device 20 may be better equipped to reliably measure a quality parameter of a harvested crop. The system 1 is adapted to be carried by a harvesting device H, such as a chopper or a combine, for example, such that the system 1 may enable the sensor device 20 to be used and/or quality-controlled while the sensor device 20 is being carried through a relatively harsh agricultural environment (such as, for example, a growing field and/or research plot) characterized by the presence of dust, extreme temperatures, high relative humidity, and changing light levels. As one skilled in the art will appreciate, such environmental parameters may be detrimental to the measurement capabilities of some sensor devices (such as near-infrared reflection (NIR) devices, for example). Thus, system 1 embodiments of the present invention provide a sensor device enclosure 10 configured to contain the sensor device 20 in a controlled environment 30 defined by at least one environmental parameter that may include, but is not limited to: temperature; humidity; light; and combinations of such parameters. As described herein, the sensor device 20 may be configured to be capable of measuring at least one quality parameter of a harvested crop 50 including, but not limited to, moisture, starch content, oil content, sugar content, protein content, digestibility, neutral detergent fiber content, and combinations thereof. According to some embodiments (such as embodiments wherein the sensor device 20 comprises an NIR device), the quality parameter may comprise a reflectance value of the harvested crop 50 (which may correspond to one or more of moisture, starch content, oil content, sugar content, protein content, digestibility, and/or neutral detergent fiber content of the harvested crop). According to such embodiments, the system 1 may comprise a computer 6 wherein the computer 6 is capable of determining one or more quality parameters of the harvested crop 50 based on a detected reflectance. In some embodiments, the computer 6 may be integrated with and/or in communication with the controller 5 described herein (wherein the controller 5 may disposed in a cab C of the harvesting device H, for example). As described further herein with respect to FIG. 3, the controller 5 may be configured to be capable of controlling the process of determining one or more quality parameters of the harvested crop 50 as well as controlling the process of referencing and validating the sensor device in either automated or manual mode.

As described herein, in some system 1 embodiments, the sensor device 20 may comprise a NIR (or VIS-NIR or UV-VIS-NIR or any other region of the electromagnetic spectrum suited to determine constituent content of harvested crops or other matrices). Measurements (such as reflectance) obtained from an NIR device may provide an accurate and relatively inexpensive method for analyzing agricultural materials such as grain or forage in terms of quantifiable quality parameters. According to such embodiments, the NIR device 20 is configured to project light on an object, such as the harvested crop 50, for example, and/or one or more components of the verification device 60. Some of the light incident on the harvested crop 50 (and/or the verification device 60), in turn, reflects off the object to the sensor device 20 which then generates a reflectance value that may be indicative of one or more quality parameters as described herein. While, some system 1 embodiments of the present invention are described herein in the context of a sensor device 20 comprising an NIR device, it should be understood that other sensor devices 20 may also be used to measure one or more quality parameters of the harvested crop 50. For example, according to various system 1 embodiments of the present invention, the sensor device 20 may comprise one or more sensors including, but not limited to: a moisture sensor, a sonar device, a light sensor, a photo detector, or a sensor device utilizing Fourier Transform infrared radiation to measure a quality parameter.

As shown generally in FIG. 1, the sensor device 20 may be mounted on and/or carried by a harvesting device H relative to a conveyance channel 40 that may be capable of delivering the harvested crop 50 (and/or a sampling thereof) to the sensor device enclosure 10 (and/or to a position adjacent to the enclosure 10 (as shown generally in FIG. 2)). For example, the arrows shown in FIG. 1 indicate the flow direction of the harvested crop 50 through the conveyance channel 40 (and consequently to a position adjacent to the sensor device enclosure 10 and/or a transparent portion 11 thereof) and to a measuring position 100 (see FIG. 2, for example) relative to the sensor device 20. As shown in FIG. 1, the sensor device enclosure 10 may be carried by the harvesting device H and positioned relative to the conveyance channel 40 (such as a spout or chute, for example) such that a number of individual grains and/or other particles of the harvested crop 50 pass substantially in front of a transparent portion 11 of the sensor device enclosure 10. The transparent portion 11 may, in some embodiments, comprise a substantially scratch-resistant material such as glass or sapphire, for example. Thus, the sensor device 10 may be capable of determining a quality parameter of a harvested crop 50 by computing an average quality parameter (and/or an average reflectance, as described further herein) for a number of individual grains and/or other particles of the harvested crop 50 as they pass substantially through a measuring position 100 disposed substantially adjacent to the transparent portion 11 of the sensor device enclosure 10 (as shown, for example, in FIG. 2). For example, the system 1 may comprise a computer 6 configured to be capable of computing an average quality parameter (and/or an average reflectance corresponding to such a quality parameter) of the harvested crop 50 as individual grains and/or other particles of the harvested crop 50 pass substantially through a measuring position 100. In some embodiments, the computer 6 may be integrated with and/or in configured to be in communication with the controller 5 described herein with reference to FIG. 3.

Various system 1 embodiments of the present invention may comprise other conveyance mechanisms for delivering the harvested crop 50 (and/or a sample, thereof) to a measuring position 100 (see FIG. 2, for example) relative to the sensor device 20. For example, in some embodiments, the sensor device enclosure 10 may be carried by a harvesting device H such that the measuring position 100 of the sensor device 20 (see FIG. 2, for example) is substantially adjacent to an output of the harvesting device (such as an output chute, channel (see element 40, for example), or other conveyance mechanism for carrying the harvested crop 50 from an output of the harvesting device H to a container (which may also be carried by the harvesting device H and/or by a support vehicle configured to accompany the harvesting device H in the agricultural environment. Thus, the harvested crop 50 may be conveyed (via the output, for example) to and/or through the measuring position 100 as described further herein. In other embodiments, the sensor device enclosure 10 may be carried by a harvesting device H such that the measuring position 100 of the sensor device 20 is substantially adjacent to (directly above, for example) a conveyor 200 (see FIG. 1) carried by the harvesting device H or adjacent to (directly beside, for example) a conveyance path disposed between a hopper 201 (or weighing bin) and the conveyor 200 such that the sensor device 20 may be capable of measuring the quality parameter of a harvested crop 50 as it falls from the hopper 201 and onto the conveyor 200.

According to some such embodiments, the actuator device 25 described herein may be used to convey the verification device 60 (such as the reference tiles 70, 80 and/or validating check cells 110, as described further herein) relative to the measurement position 100 of the sensor device 20 such that the sensor device 20 may be positioned substantially stationary relative to the conveyor 200 (and/or relative to a measurement position 100 disposed between a hopper 201 and a the conveyor 200) carried by the harvesting device H and such that the sensor device 20 may still be referenced and/or validated as described further herein without the need to move and/or actuate the sensor device 20 relative to the measuring position 100.

As shown in FIGS. 1 and 2, the system 1 comprises a verification device 60 disposed within the sensor device enclosure 10. The verification device 60 may be characterized by a known parameter that is comparable and/or readily convertible to an output of the sensor device 20 such that the sensor device 20 may be referenced and/or validated by measuring some parameter of the verification device 60. The term "verification device" 60 as used herein, may refer generally to devices capable of performing both referencing (including, but not limited to "zeroing") functions and validation functions. For example the "verification device" 60 may comprise reference tiles 70, 80 for establishing zero, 100%, and/or other reference reflectance values in embodiments wherein the sensor device 20 comprises an NIR device. Furthermore, the term "verification device," 60 as used herein, may also refer generally to one or more validation check cells 110 (containing validation crop samples 90, for example, as shown in FIG. 2) for validating the operation of the sensor device 20. For example, each of the check cells 110 may contain validation crop samples 90 having a known reflectance value or other known parameter. Thus, when the sensor device 20 is conveyed to a position substantially adjacent to one of the check cells 110, the known parameter of the check cell (which may be stored in a memory device integrated with the computer 6 and/or the controller 5 in communication with the system 1) may be directly compared (using the output of chemometric software carried by a computer 6, for example) with the measured parameter output of the sensor device such that the sensor device 20 may, in turn, be validated in the field.

For example, in system 1 embodiments wherein the sensor device 20 comprises a NIR device, the verification device 60 may comprise one or more reference tiles (such as, for example, a black reference tile 70 for establishing a "substantially no reflectance" and a white reference tile 80 for establishing a "100% reflectance" value for the NIR device so as to "zero" the NIR device. In embodiments wherein the sensor device 20 comprises a NIR device, the term "zeroing" may be defined generally as both: establishing a zero reflectance value standard for the sensor device 20 (by scanning a black reference tile 70, for example); and also establishing a 100% reflectance value for the sensor device 20 (by scanning a white reference tile 80). Furthermore, and as described herein, according to some embodiments, the verification device 60 may further comprise a validation crop sample 90 (see FIG. 2, for example) characterized by a known parameter that may include, but is not limited to: a moisture content of the validation crop sample 90; a starch content of the validation crop sample 90; an oil content of the validation crop sample 90; a sugar content of the validation crop sample 90; a protein content of the validation crop sample 90; a digestibility measure of the validation crop sample 90; a neutral detergent fiber (NDF) content of the validation crop sample 90; and combinations of such parameters. Thus, a reflectance value of the validation crop sample 90 (as produced by a sensor device 20 such as a NIR device, for example) may be used to validate the sensor device 20 such that the output of the sensor device 20 may be readily and reliably converted (by a controller 5, for example or a separate computer 6 in communication with the system 1) to one or more quality parameters corresponding to a harvested crop 50. In some system 1 embodiments, the sensor device 20 may comprise a computer 6 either in communication with the sensor device 20 and/or integrated with the sensor device 20 for storing verification measurements and/or conversion factors in a memory device (that may be in communication with and/or integrated with the computer 6). According to such embodiments, the computer 6 may be further configured to be capable of calculating one or more conversion factors (i.e. reflectance to quality parameter conversions using commercially-available chemometric software) based on the interaction of the sensor device 20 with one or more verification devices 60. In some such embodiments, the computer 6 may be integrated with and/or in communication with the controller 5 described herein with reference to FIG. 3.

In some system 1 embodiments, as shown generally in FIG. 2, the validation crop samples 90 may be contained within corresponding check cells 110. To maintain the chemical, physical, and/or reflectance properties of the validation crop sample 90 at a substantially constant state, the check cell 110 may comprise a substantially transparent and/or substantially fluid-tight material such as, for example, polycarbonate and/or glass. Thus, according to such embodiments, the check cell 110 may prevent the validation crop sample 90 from being exposed to the elements (moisture, dust, and/or ambient air, for example) that may cause the physical properties of the validation crop sample 90 to change over time (which may, in turn, result in a change in a reflectance value of the validation crop sample 90).

Various system 1 embodiments of the present invention, as shown generally in FIG. 2, may further comprise an actuator device 25 configured to selectively convey the sensor device 20 to a measuring position 100 such that the sensor device 20 is capable of measuring desired parameters of the harvested crop 50. The actuator device 25 is also configured to selectively convey the sensor device 20 to a verification position substantially adjacent to the verification device 60 (such as, for example, the reference tiles 70, 80 and/or one or more check cells 110). In this regard, the sensor device 20 may be validated and/or "zeroed" by comparing the known parameter of the verification device 60 to a verification parameter measured by the sensor device 20 when the sensor device 20 is selectively conveyed to one or more verification position(s) (see elements 70, 80, 110 of FIG. 2, for example). In the embodiment shown in FIG. 2, the arrows indicate selective conveyance of the sensor device 20 above the various components of the verification device 60 and above the measuring position 100. For example, in the embodiment shown in FIG. 2, the actuator device 25 is configured to be capable of conveying the sensor device 20 to one of five discrete positions (including, for example, the measuring position 100 and four verification positions relative to the various components 70, 80, 110 of the verification device 60. In various other system 1 embodiments, the actuator device 25 may be configured to convey the sensor device 20 to a number of different distinct positions (such as, for example, two to eight discrete locations relative to the actuator track 28 of the linear actuator device 25 such that the actuator device 25 is capable of precisely conveying the sensor device 20 to each of number of components of the verification device 60 and a number of measuring positions 100.

As shown in FIG. 2, the actuator device 25 may comprise a linear actuator device for conveying the sensor device to the measuring position 100 and/or at least one of the verification positions 70, 80, 90 wherein the various verification positions 70, 80, 90 are disposed substantially in series with the measuring position 100. For example, the linear actuator device 25 may comprise an actuator bearing track 28 such that the sensor device 20 may be slidable relative to the bearing track 28. The actuator device 25 may further comprise a screw drive 27 (such as a jack screw, for example) operably engaged with a motor 26 (such as a stepper motor, for example) for rotating the screw drive 27 (in response to control inputs (see FIG. 3, for example) from the controller 5, for example). Thus, the linear actuator device 25 may be capable of precisely conveying the sensor device 20 to one or more of the verification positions 70, 80, 90 and/or to the measuring position 100.

As shown in FIG. 2, the actuator device 25 may further comprise a plurality of adjustable stops 29 corresponding to a plurality of discrete positions including at least one of the measuring position 100 and one or more of the verification positions 70, 80, 90. The linear actuator device 25 may be configured to be responsive to the adjustable stops 29 so as to be capable of conveying the sensor device 20 precisely and repeatably to each of the plurality of discrete positions within the sensor device enclosure 10. The adjustable stops 29 may, in some system 1 embodiments, comprise set screws and/or other fastening mechanisms that may allow a user to precisely adjust the position of the adjustable stops 29 relative to the actuator device 25 (and/or a bearing track 28 thereof).

The various sensor device 20 types that may be used to measure a quality parameter of a harvested crop 50 may each benefit from the precision motion and placement afforded by an actuator device 25 that is capable of precisely and accurately conveying the sensor device 20 to a measuring position 100 relative to the harvested crop 50 and/or to a verification position relative to one or more components 70, 80, 90 of a verification device 60. Thus, some system 1 embodiments of the present invention may comprise an actuator device 25 comprising various types of precision linear actuator devices 25, including, but not limited to: voltage-controlled screw-drive actuators (such as the screw drive 27 shown generally in FIG. 2, for example); electromechanical pistons in communication with a controller 5; hydraulic pistons in communication with a hydraulic manifold and/or controller 5; piezoelectric linear actuators; and/or combinations of such actuator devices.

In the embodiment shown in FIG. 2, the sensor device 20 may be conveyed substantially linearly to a verification position substantially adjacent to at least one of: the black reference tile 70, the white reference tile 80, the check cells 110, and/or the measuring position 100. According to this and some other system 1 embodiments, the sensor device 20 may be conveyed substantially horizontally and/or substantially parallel to a horizontal plane (defined, for example, by the bearing track 28 of the actuator device 25). However, other system 1 embodiments of the present invention may further comprise an actuator device 25 configured to be capable of conveying the sensor device 20 in a variety of different directions and/or orientations such that the sensor device 20 may be precisely positioned adjacent to and/or relative to a selected discrete number of verification and/or measurement positions. Furthermore, and as described herein, one or more of the verification devices 60 may also be operably engaged with and/or carried by the actuator device 25 such that the sensor device 20 may be carried in a substantially static position relative to the measuring position 100. Thus, the actuator device 25 may be similarly capable of conveying one or more of the reference tiles 70, 80 and/or the validation crop samples 90 to the measurement position 100 such that the sensor device 20 need not be moved relative to the harvesting device H.

Figure 6:
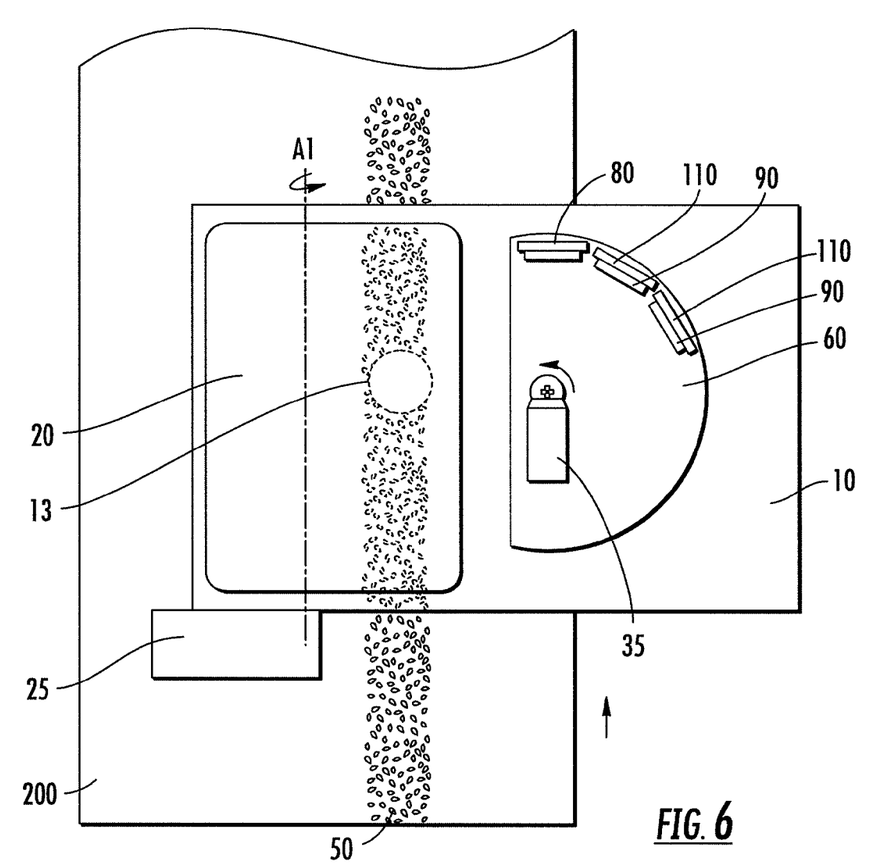
FIG. 6 shows a schematic detailing a sensor device and a verification device, wherein the sensor device is in a measuring location according to one embodiment of the present invention.
Figure 6A:
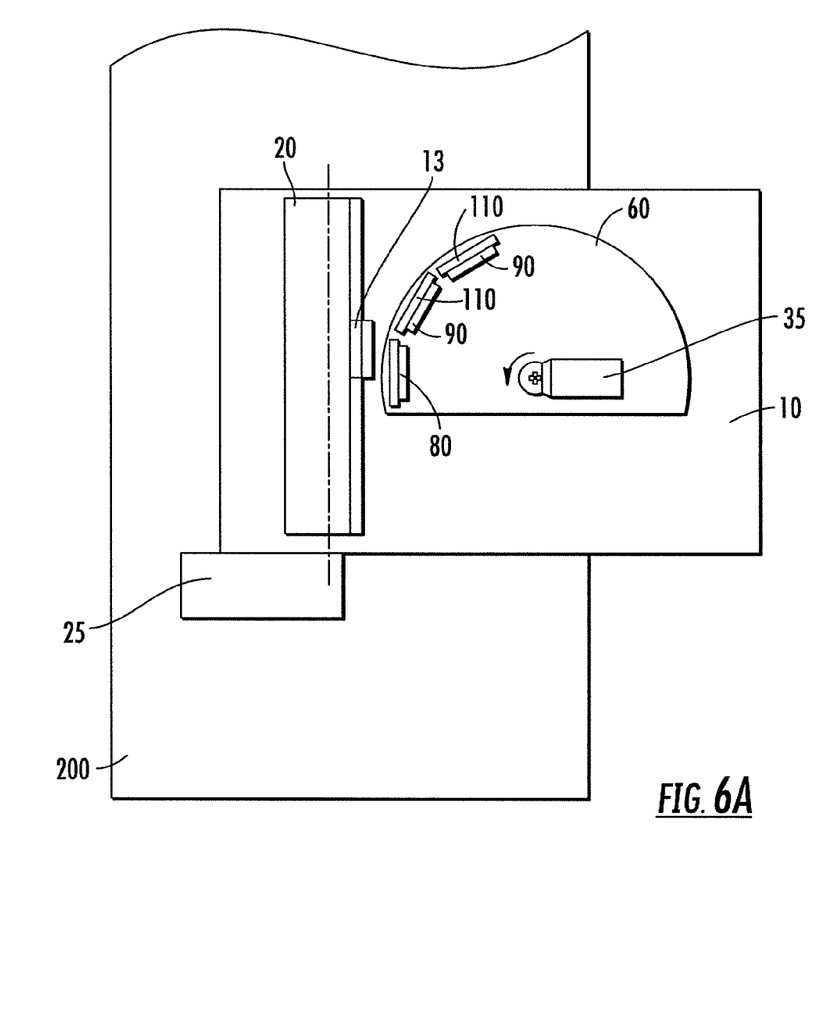
FIG. 6A shows a schematic detailing a sensor device and a verification device, wherein an actuator has rotated the sensor device to a verification location according to one embodiment of the present invention.

Additional configurations may include, but need not be limited to, configurations where the sensor device and/or the verification device are rotated (such as, for example, using a stepper motor or other similar device capable of relatively accurate positioning) such that the sensor device may be positioned adjacent to and/or relative to a selected number of verification and/or measurement positions. An example of such a configuration is shown in FIGS. 6 and 6A. As shown in these figures, a sensor device 20 (which in the depicted embodiment is a NIR device) is disposed within a sensor device enclosure 10, which may be carried by the harvesting device H such that a measuring position of the sensor device 20 is substantially adjacent to a conveyor 200. The conveyor 200 may be capable of delivering the harvested crop 50 (and/or a sampling thereof) to a position adjacent to the enclosure 10 such that the harvested crop 50 passes underneath a position adjacent a lens portion 13 of the sensor device 20. Thus, as above, the sensor device 20 may be capable of determining a quality parameter of a harvested crop 50 by computing an average quality parameter (and/or an average reflectance, as described further herein) for a number of individual grains and/or other particles of the harvested crop 50 as they pass substantially through a measuring position disposed substantially adjacent to the lens portion 13 of the sensor device enclosure 10.

As noted above, a verification device 60 may be characterized by a known parameter that is comparable and/or readily convertible to an output of the sensor device 20 such that the sensor device 20 may be referenced and/or validated by measuring some parameter of the verification device 60. For example, as shown in FIG. 6, the verification device 60 may comprise one or more reference tiles (such as, for example, a black reference tile 70 for establishing a "substantially no reflectance" and a white reference tile 80 for establishing a "100% reflectance" value for the NIR device so as to "zero" the NIR device). Furthermore, in the depicted embodiment, the verification device 60 may also comprise check cells 110 that may contain validation crop samples 90. As above, the validation crop samples 90 may be characterized by a known parameter that may include, but is not limited to: a moisture content of the validation crop sample 90; a starch content of the validation crop sample 90; an oil content of the validation crop sample 90; a sugar content of the validation crop sample 90; a protein content of the validation crop sample 90; a digestibility measure of the validation crop sample 90; a neutral detergent fiber (NDF) content of the validation crop sample 90; and combinations of such parameters. Thus, a reflectance value of the validation crop sample 90 may be used to validate the sensor device 20 such that the output of the sensor device 20 may be readily and reliably to one or more quality parameters corresponding to a harvested crop 50.

As shown generally in FIG. 6, an actuator device 25 is configured to selectively rotate the sensor device 20 (such as, for example, using a stepper motor and one or more gears) about axis A1 between a measuring position such that the sensor device 20 is capable of measuring desired parameters of the harvested crop 50 and a verification position (shown in FIG. 6A) in which the lens portion 13 of the sensor device 20 is substantially adjacent to the verification device 60. Once in the verification position, a second actuator device 35 may rotate the verification device 60 (such as, for example, using a stepper motor and one or more gears) so that reference tile 80 and check cells 110 containing reference samples 90 may be individually positioned adjacent the lens portion 13 of the sensor device 20. In this regard, the sensor device 20 may be validated and/or "zeroed" by comparing the known parameter of the verification device 60 to a verification parameter measured by the sensor device 20 when the sensor device 20 is selectively rotated to the individual verification positions.

Figure 3:
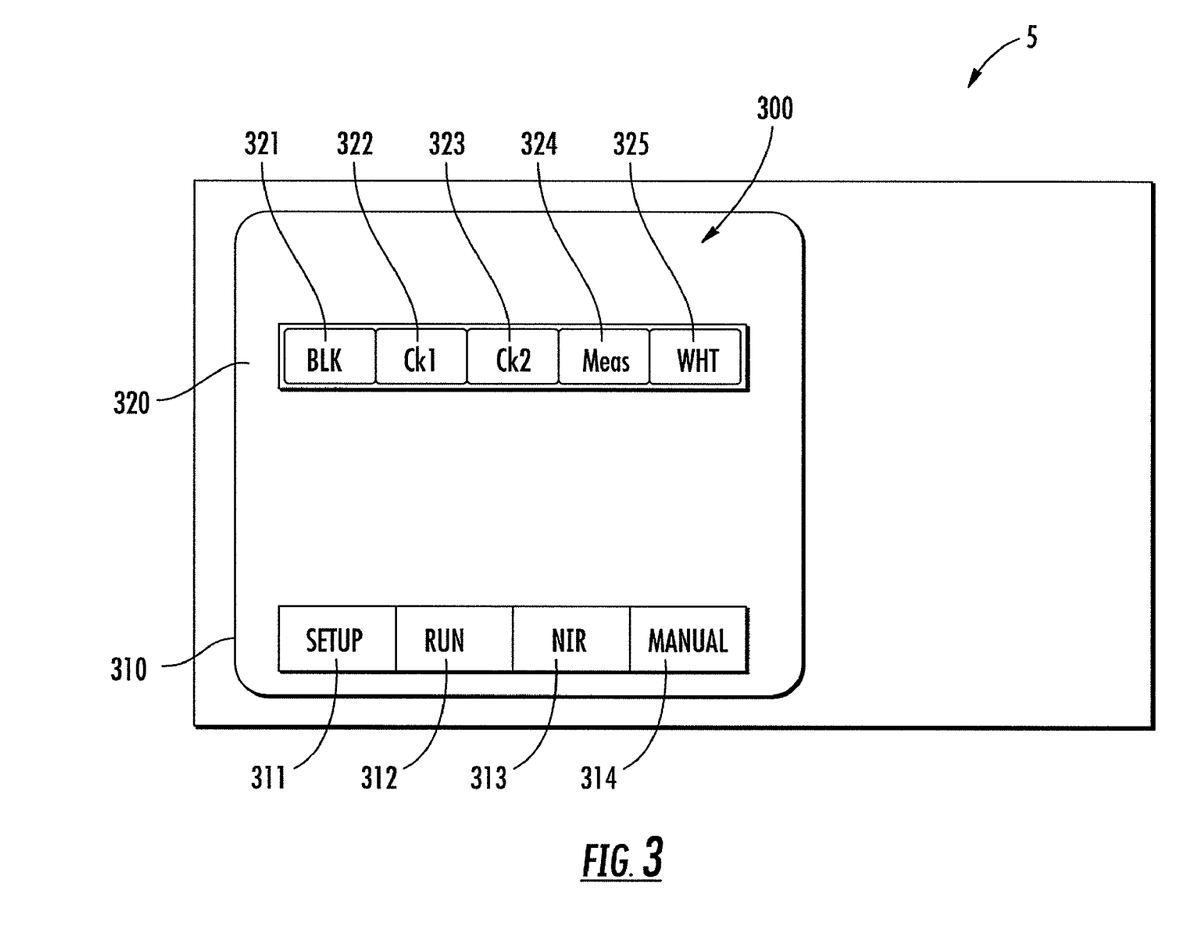
FIG. 3 shows a schematic view of a display generated by a controller device in communication with the enclosed system, according to one embodiment of the present invention.

As described herein with respect to FIG. 3, the actuator device 25 may be in communication with a controller 5 capable of receiving a user input (via a touch screen display 300, for example, as shown generally in FIG. 3). According to various embodiments, such user inputs may include a selection of a linear or rotation position including, but not limited to: a particular measurement position 324; a verification position 321 (corresponding to the position of the black reference tile 70, for example); a verification position 322 (corresponding to the position of a first check cell 110, for example); a verification position 323 (corresponding to the position of a second check cell 110, for example); and a verification position 325 (corresponding to the position of the white reference tile 80, for example).

In other embodiments, the controller may be configured to be capable of running a predetermined program for periodically instructing the actuator device 25 to convey the sensor device 20 to a referencing and/or verification position as the system 1 of the present invention is conveyed (by a harvesting device H, for example) through an agricultural environment. For example, the controller 5 may comprise a display 300 (such as a touch-screen display, for example) including a number of input controls 310 that may include, but are not limited to a setup button 311 (wherein a user may specify a triggering event and/or an interval after which the actuator device 25 may convey the sensor device 20 from the measurement position 100 to one or more verification positions 60 for referencing and/or validating the operation of the sensor device 20). The input controls 310 may further comprise a run button 312 allowing a user to initiate an automated and/or substantially pre-determined program of conveyance steps for referencing and/or validating the sensor device 20. The display 300 of the controller 5 may further include an "NIR" or other sensor device 20 button 313 for initiating the display of a status of the sensor device 20 and/or for initiating the display of a sensor device 20 "control panel" (not shown), wherein a user may input a variety of manual adjustments to the measurement parameters of the sensor device 20. Furthermore, as shown in FIG. 3, the display 300 of the controller 5 may further include a "manual" button 314 wherein a user may initiate the substantially manual selection of a particular measurement position 100 and/or one or more verification positions 70, 80, 90. Thus, according to such embodiments, the user may select the "manual" button 314 and subsequently select one of the position buttons 320 and thereby instruct the actuator device 25 to immediately convey the sensor device 20 to a selected position corresponding to one or more of the position buttons 320 (including, but not limited to: the measurement position 324; the verification position 321 (corresponding to the position of the black reference tile 70, for example); the verification position 322 (corresponding to the position of a first check cell 110, for example); the verification position 323 (corresponding to the position of a second check cell 110, for example); and the verification position 325 (corresponding to the position of the white reference tile 80, for example). As described generally herein with respect to FIG. 2, a user may manually adjust the physical position of the sensor device 20 corresponding to the selection of a particular position button 320 by slidably adjusting and/or selectively securing one or more of the plurality of adjustable stops 29 corresponding to a plurality of discrete positions within the sensor device enclosure 10 (including at least one of the measuring position 100 and one or more of the verification positions 70, 80, 90).

In this regard, the actuator device 25 (using control inputs generated and/or received by the controller 5, for example) may be configured to be capable of selectively and precisely conveying the sensor device 20 to one or more verification and/or referencing positions substantially adjacent a black reference tile 70 and/or substantially adjacent a white reference tile 80. Thus, in embodiments wherein the sensor device 20 comprises a NIR device, the sensor device 20 may be configured to be capable of determining the reflectance values of the reference tiles 70, 80 to "zero" and/or "reference" the sensor device 20. In a similar manner, the actuator device 25 may be configured to be capable of conveying the sensor device 20 to a position adjacent to one or more check cells 110, such that the sensor device 20 (comprising a NIR device, for example) may again determine a reflectance at each check cell 110 (corresponding to a "verification measurement"). The reflectance recorded from the crop sample 90 associated with each check cell 110 may then be compared with a predicted validation parameter value and, if within statistical limits, the sensor device 20 may be "validated" (i.e. determined to be operating within its specifications). According to some embodiments, the sensor device 20 may also be adjusted (using, for example, a sensor device 20 "control panel" accessed via the "NIR" button 313 generated by the display 300 of the controller 5) such that the verification parameter measured by the sensor device 20, while the sensor device 20 is disposed in a verification position, substantially matches the known parameter of the verification device 60. Once the sensor device 20 is properly referenced (with respect to one or more reference tiles 70, 80) and validated to a reference standard (with respect to one or more validation crop samples 90), the actuator device 25 may then selectively move the sensor device 20 to a position adjacent to the harvested crop 50 and/or substantially above a measuring position 100, where the sensor device 20 may be capable of measuring a quality parameter (characterized, in some embodiments, as a characteristic reflectance) of the harvested crop 50.

Figure 4:
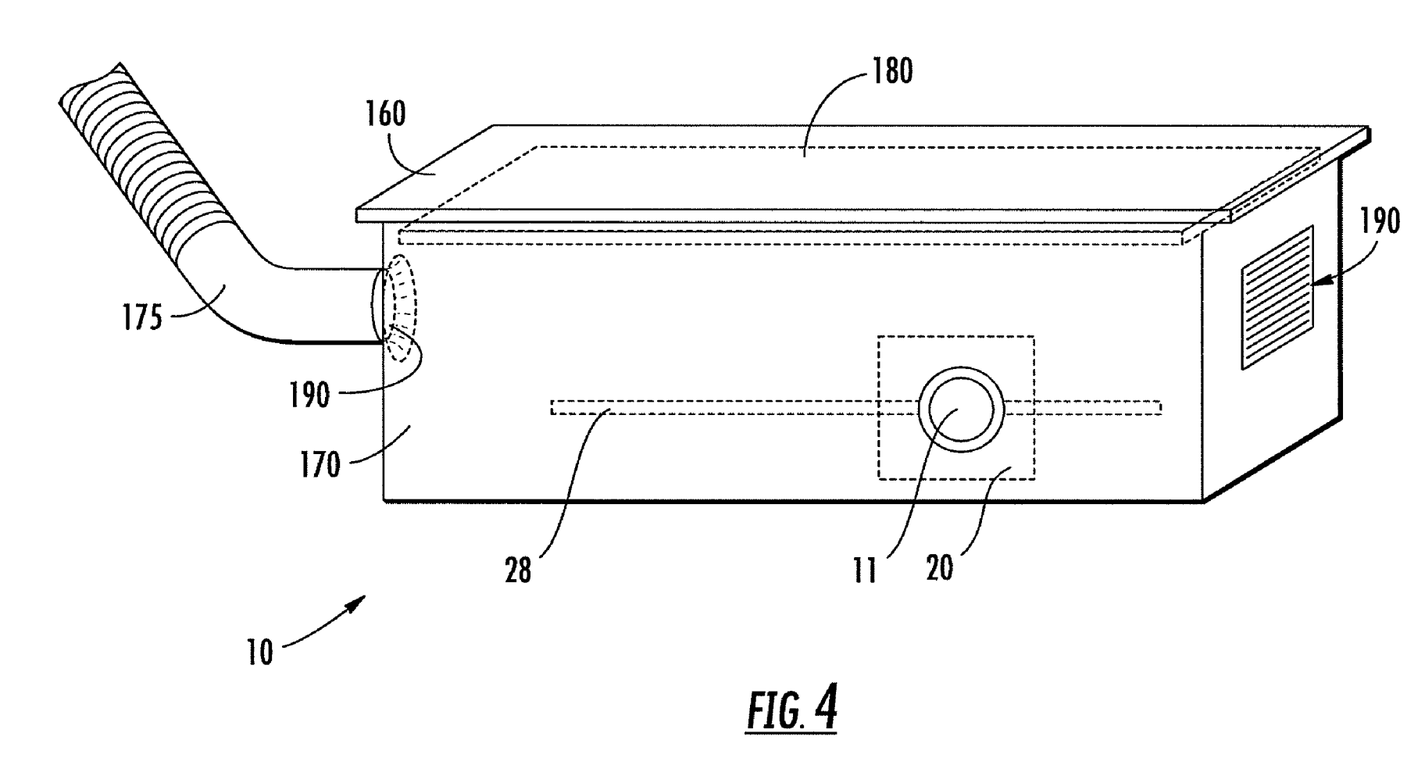
FIG. 4 shows a perspective view of a sensor device enclosure highlighting features allowing for a controlled environment therein, according to one embodiment of the present invention.

As shown generally in FIG. 4, the system 1 embodiments of the present invention may comprise a sensor device enclosure 10 configured to be capable of containing the sensor device 20 in a controlled environment 30 defined by at least one environmental parameter. According to various embodiments, the sensor device enclosure 10 may include one or more features, individually or in combination, such that the sensor device 20 is enclosed in the controlled environment 30 defined by at least one environmental parameter, such as, for example, temperature, humidity, light, and combinations thereof. As shown generally in FIG. 4, the sensor device enclosure 10 may comprise substantially light-reflective material 160 disposed on an outer surface of the sensor device enclosure (such as, for example, a polyurethane paint with a light reflectance value greater than 0.8) for preventing the accumulation of heat within the sensor device enclosure 10. In addition, the sensor device enclosure 10 may comprise insulation material 170 (such as, for example, high-density molded expanded polystyrene, with an approximate R-value of 4) such that heat transfer between an interior of the sensor device enclosure and an exterior of the sensor device enclosure is substantially reduced and/or minimized. The insulation material may also comprise high R-value or "super insulating" materials (such as, for example, vacuum-insulated panels (VIPs). The sensor device enclosure 10 may further comprise one or more transparent portions 11 (such as, for example, a substantially transparent window) corresponding substantially to the measurement position 100 shown, for example, in FIG. 2. Specifically, the sensor device enclosure 10 may define one or more measurement position 100 apertures (see, for example the transparent portion 11 shown in FIG. 4) such that the sensor device 20 may be capable of illuminating the harvested crop 50 and/or detecting a resultant characteristic reflectance of the harvested crop 50 when the sensor device 20 is conveyed the measurement position 100. In order to maintain the insulating capacity of the sensor device enclosure 10 (and such that the at least one environmental parameter characterizing the controlled environment 30 therein may be effectively maintained), the transparent portion 11 of the sensor device enclosure 10 may comprise double-pane, high R-value glass and/or polycarbonate that may allow the sensor device 20 to measure the quality parameter of the harvested crop 50 as it passes a measurement position 100 without compromising the controlled environment 30 of the interior of the sensor device enclosure 10. In some embodiments, the transparent portion 11 of the sensor device enclosure 10 may comprise a substantially scratch-resistant material including, but not limited to glass and sapphire crystal such that the harvested crop 50 and accompanying debris is less likely to scratch and/or damage the transparent portion 11.

Furthermore according to some embodiments, an air-conditioning device 180 may be operably engaged with the sensor device enclosure 10. The air conditioning device 180 may be in fluid communication with the sensor device enclosure via at vent aperture (see, for example, element 190) defined in the sensor device enclosure 10. The air-conditioning device 180 is configured to control the at least one environmental parameter (such as temperature and/or humidity, for example). As described herein, the sensor device enclosure 10 may further define a vent aperture 190. The vent aperture 190 may be configured to be operably engaged with a conduit 175 for conveying an air flow to alter the at least one environmental parameter. For example, the vent aperture 190 may be operably engaged with HVAC ducts leading to a fan and/or a dedicated air conditioning device 180. In other embodiments, the vent aperture 190 may be in fluid communication with a duct in further fluid communication with an air-conditioned interior of an operator cab C of the harvesting device H, for example. It should be understood that other environmental conditioning mechanisms may be utilized to maintain the sensor device 20 in the controlled environment 30. For example, in some embodiments, the sensor device enclosure 10 may include plumbing through which a coolant liquid may be introduced and/or circulated to maintain the controlled environment 30. Furthermore, according to some embodiments, as shown generally in FIG. 4, the air-conditioning device 180 may comprise a cooling device (such as a cooling plate, radiator, and/or heat sink, for example) configured to be capable of reducing a temperature within the sensor device enclosure 10.

Additional embodiments may further provide a method for measuring a quality parameter of a harvested crop. According to one method embodiment, shown schematically in FIG. 5, the method first comprises step 510 for enclosing a sensor device 20 in a sensor device enclosure 10 configured to contain the sensor device 20 in a controlled environment defined by at least one environmental parameter. The method further comprises step 520 for conveying the sensor device 20 to a verification position substantially adjacent to a verification device 60. As described herein with respect to the various system 1 embodiments of the present invention, the verification device 60 is disposed substantially within the sensor device enclosure 10 such that the sensor device 20 may be calibrated without interference from potentially error-inducing environmental conditions, including, but not limited to: high concentrations of dust, extreme temperatures, high humidity levels, and excessive ambient light levels. As described herein, the verification device 60 disposed within the sensor device enclosure 10 is characterized by a known parameter (such as, for example, a known reflectance and/or other known quantifiable and/or identifiable physical parameter).

Figure 5:
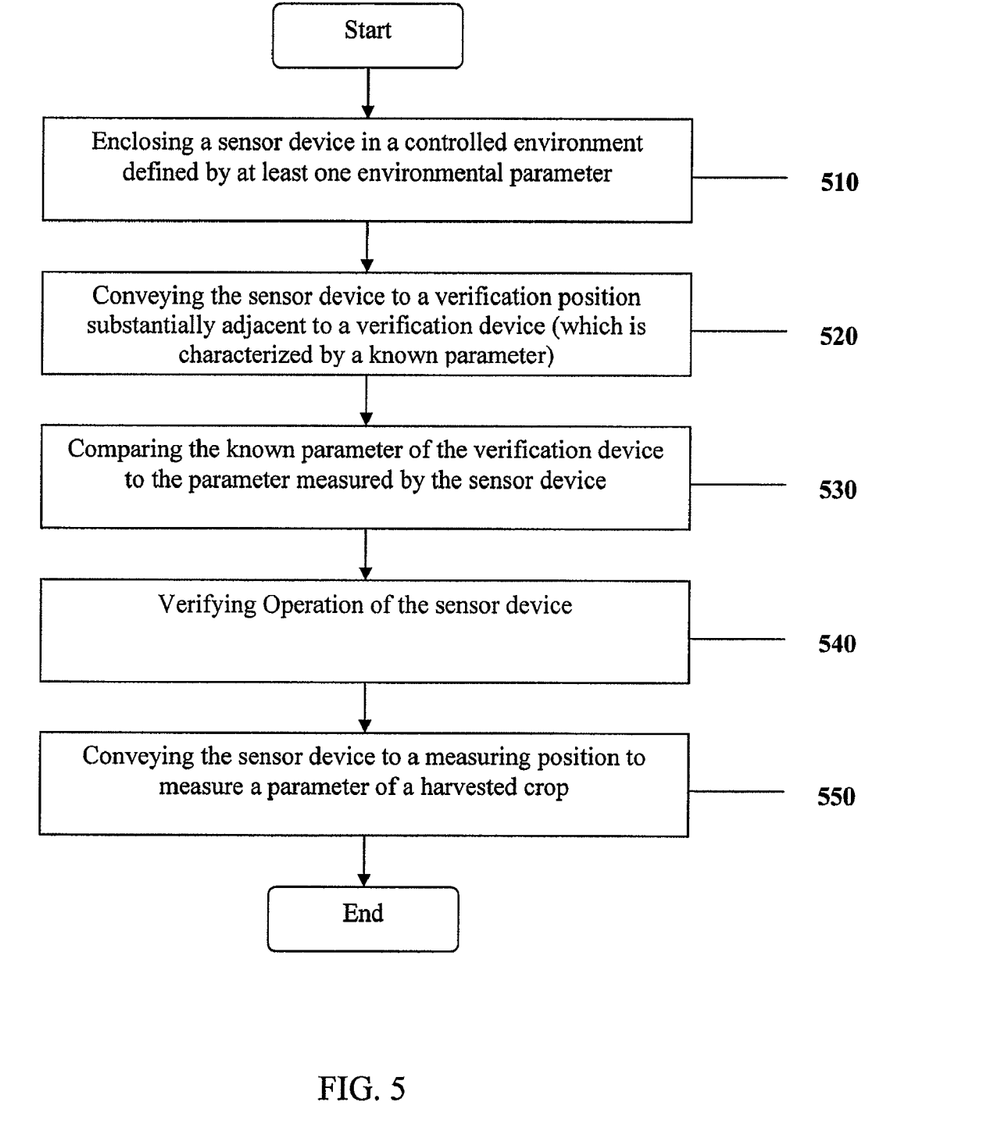
FIG. 5 shows a flow chart of a method for measuring a parameter of a harvested crop, according to one embodiment of the present invention.

As shown in FIG. 5, the method further comprises step 530 for comparing the known parameter of the verification device 60 to a verification parameter measured by the sensor device 20 when the sensor device (and/or the verification device 60) is conveyed to one or more verification positions (adjacent and/or relative to one or more components of the verification device 60, as described herein). Step 540 comprises verifying the operation of the sensor device 20 by controlling the lower and upper acceptable limits of the differences between the known and measured parameters of moisture and other constituent contents (step 530, for example).

The method embodiments of the present invention further comprise step 550 for conveying the sensor device 20 to a measuring position (see element 100, FIG. 2, for example) relative to the harvesting device such that the sensor device 20 is capable of measuring a quality parameter of the harvested crop 50. As described herein with respect to the various system 1 embodiments of the present invention, the various conveying steps (520 and 550, for example) may be accomplished using an actuator device 25 configured to be capable of precisely conveying the sensor device 20 to one or more measurement and/or verification positions disposed substantially within the sensor device enclosure 10 (see FIG. 2, for example). For example, step 550 for conveying the sensor device 20 to a measuring position 100, may comprise conveying the sensor device 20 to a position substantially adjacent to a window or other substantially transparent portion 11 of the sensor device enclosure 10 (see FIG. 4) such that the sensor device 20 may be capable of measuring a quality parameter of a harvested crop 50 that may be conveyed adjacent to a transparent portion 11 and/or through a port defined in the sensor device enclosure 10.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system for measuring a quality parameter of a harvested crop, the system adapted to be carried by a harvesting device such that the sensor device is capable of measuring the quality parameter of a harvested crop, the system comprising:
a sensor device enclosure configured to contain the sensor device in a controlled environment defined by at least one environmental parameter;
a verification device disposed within the sensor device enclosure, the verification device being characterized by a known parameter;
an actuator device configured to selectively convey the sensor device to a measuring position relative to the harvesting device such that the sensor device is capable of measuring the quality parameter of the harvested crop, the actuator device being further configured to selectively convey the sensor device to a verification position substantially adjacent to the verification device such that the sensor device is capable of measuring a verification parameter of the verification device so as to verify an operating capacity of the sensor device by comparing the known parameter of the verification device to the verification parameter measured by the sensor device when the sensor device is conveyed to the verification position.

2. The system according to claim 1, wherein the verification device is selected from the group consisting of:
a reference tile;
a validation crop sample; and
combinations thereof.

3. The system according to claim 2, wherein the reference tile is selected from the group consisting of:
a black reference tile characterized by the known parameter including a reflectance value of substantially zero;
a white reference tile characterized by the known parameter including a known non-zero reflectance value; and
combinations thereof.

4. The system according to claim 2, wherein the known parameter is selected from the group consisting of:
a reflectance of the verification device;
a moisture of the validation crop sample;
a starch content of the validation crop sample;
an oil content of the validation crop sample;
a sugar content of the validation crop sample;
a protein content of the validation crop sample;
a digestibility measure of the validation crop sample;
a neutral detergent fiber content of the validation crop sample;
and combinations thereof.

5. The system according to claim 1, wherein the sensor device enclosure comprises a substantially light-reflective material disposed on an outer surface of the sensor device enclosure.

6. The system according to claim 1, wherein the sensor device enclosure comprises an insulating material such that heat transfer between an interior of the sensor device enclosure and an exterior of the sensor device enclosure is minimized.

7. The system according to claim 1, further comprising an air-conditioning device operably engaged with the sensor device enclosure and in fluid communication with the sensor device enclosure via a vent aperture defined in the sensor device enclosure, the air-conditioning device configured to control the at least one environmental parameter.

8. The system according to claim 1, wherein the sensor device enclosure defines a vent aperture, the vent aperture being configured to be operably engaged with a conduit for conveying an air flow to alter the at least one environmental parameter.

9. The system according to claim 7, wherein the at least one environmental parameter is selected from the group consisting of:
temperature;
humidity;
light level;
dust concentration;
and combinations thereof.

10. The system according to claim 8, wherein the at least one environmental parameter is selected from the group consisting of:
temperature;
humidity;
light level;
dust concentration;
and combinations thereof.

11. The system according to claim 1, wherein the actuator device comprises a linear actuator device for conveying the sensor device to at least one of the measuring position and the verification position.

12. The system according to claim 11, wherein the linear actuator device comprises a screw drive for conveying the sensor device to at least one of the measuring position and the verification position.

13. The system according to claim 11, wherein the actuator device further comprises a plurality of adjustable stops corresponding to a plurality of discrete positions including at least one of the measuring position and the verification position, and wherein the linear actuator device is configured to be responsive to the adjustable stops so as to be capable of conveying the sensor device to each of the plurality of discrete positions.

14. The system according to claim 1, wherein the actuator device comprises a rotational actuator device for conveying the sensor device to at least one of the measuring position and the verification position.

15. The system according to claim 14, further comprising a second actuator device configured to selectively convey the verification device relative to the sensor device such that the sensor device is capable of measuring one or more verification parameters of the verification device.

16. A system for measuring a quality parameter of a harvested crop, the system adapted to be carried by a harvesting device, the system comprising:
a sensor device, the sensor device being capable of measuring a quality parameter of a harvested crop;
a sensor device enclosure configured to contain the sensor device in a controlled environment defined by at least one environmental parameter;
a verification device disposed within the sensor device enclosure, the verification device being characterized by a known parameter;
an actuator device configured to selectively convey the sensor device to a measuring position relative to the harvesting device such that the sensor device is capable of measuring the quality parameter of the harvested crop, the actuator device being further configured to selectively convey the sensor device to a verification position substantially adjacent to the verification device such that the sensor device is capable of measuring a verification parameter of the verification device so as to calibrate the sensor device by comparing the known parameter of the verification device to the verification parameter measured by the sensor device when the sensor device is conveyed to the verification position.

17. The system according to claim 16, wherein the verification device is selected from the group consisting of:
   a reference tile;
   a validation crop sample; and
   combinations thereof.

18. The system according to claim 17, wherein the reference tile is selected from the group consisting of:
   a black reference tile characterized by the known parameter including a reflectance value of substantially zero;
   a white reference tile characterized by the known parameter including a known non-zero reflectance value; and
   combinations thereof.

19. The system according to claim 17, wherein the known parameter is selected from the group consisting of:
   a reflectance of the verification device;
   a moisture of the validation crop sample;
   a starch content of the validation crop sample;
   an oil content of the validation crop sample;
   a sugar content of the validation crop sample;
   a protein content of the validation crop sample;
   a digestibility measure of the validation crop sample;
   a neutral detergent fiber content of the validation crop sample;
   and combinations thereof.

20. The system according to claim 16, wherein the sensor device enclosure comprises a substantially light-reflective material disposed on an outer surface of the sensor device enclosure.

21. The system according to claim 16, wherein the sensor device comprises an insulating material such that heat transfer between an interior of the sensor device enclosure and an exterior of the sensor device enclosure is minimized.

22. The system according to claim 16, further comprising an air-conditioning device operably engaged with the sensor device enclosure and in fluid communication with the sensor device enclosure via a vent aperture defined in the sensor device enclosure, the air-conditioning device configured to control the at least one environmental parameter.

23. The system according to claim 16, wherein the sensor device enclosure defines a vent aperture, the vent aperture being configured to be operably engaged with a conduit for conveying an air flow to alter the at least one environmental parameter.

24. The system according to claim 22, wherein the at least one environmental parameter is selected from the group consisting of:
   temperature;
   humidity;
   light level;
   dust concentration;
   and combinations thereof.

25. The system according to claim 23, wherein the at least one environmental parameter is selected from the group consisting of:
   temperature;
   humidity;
   light level;
   dust concentration;
   and combinations thereof.

26. The system according to claim 16, wherein the sensor device is selected from the group consisting of:
   a near infrared reflection (NIR) device;
   a moisture sensor;
   a sonar device;
   a light sensor;
   a photo detector;
   and combinations thereof.

27. A system according to claim 16, wherein the actuator device comprises a linear actuator device for conveying the sensor device to at least one of the measuring position and the verification position.

28. A system according to claim 27, wherein the linear actuator device comprises a screw drive for conveying the sensor device to at least one of the measuring position and the verification position.

29. The system according to claim 27, wherein the actuator device further comprises a plurality of adjustable stops corresponding to a plurality of discrete positions including at least one of the measuring position and the verification position, and wherein the linear actuator device is configured to be responsive to the adjustable stops so as to be capable of conveying the sensor device to each of the plurality of discrete positions.

30. The system according to claim 16, wherein the actuator device comprises a rotational actuator device for conveying the sensor device to at least one of the measuring position and the verification position.

31. The system according to claim 30, further comprising a second actuator device configured to selectively convey the verification device relative to the sensor device such that the sensor device is capable of measuring one or more verification parameters of the verification device.

32. A method for measuring a quality parameter of a harvested crop, the method comprising:
   enclosing a sensor device in a sensor device enclosure configured to contain the sensor device in a controlled environment defined by at least one environmental parameter;
   conveying the sensor device to a verification position substantially adjacent to a verification device, the verification device disposed within the sensor device enclosure and being characterized by a known parameter;
   comparing the known parameter of the verification device to a verification parameter measured by the sensor device so as to determine a difference therebetween, when the sensor device is conveyed to the verification position;
   verifying the operation of the sensor device by comparing the difference determined in the comparing step to a selected upper limit and a selected lower limit; and
   conveying the sensor device to a measuring position relative to the harvesting device such that the sensor device is capable of measuring the quality parameter of the harvested crop.

33. The method according to claim 32, wherein the verification device is selected from the group consisting of:
   a reference tile;
   a validation crop sample; and
   combinations thereof.

34. The method according to claim 33, wherein the reference tile is selected from the group consisting of:
   a black reference tile characterized by the known parameter including a reflectance value of substantially zero;
   a white reference tile characterized by the known parameter including a known non-zero reflectance value; and
   combinations thereof.

35. The method according to claim 33, wherein the known parameter is selected from the group consisting of:
   a reflectance of the verification device;
   a moisture of the validation crop sample;
   a starch content of the validation crop sample;

an oil content of the validation crop sample;
a sugar content of the validation crop sample;
a protein content of the validation crop sample;
a digestibility measure of the validation crop sample;
a neutral detergent fiber content of the validation crop sample;
and combinations thereof.

36. The method according to claim 32, further comprising controlling the at least one environmental parameter using an air-conditioning device operably engaged with the sensor device enclosure and in fluid communication with the sensor device enclosure via a vent aperture defined in the sensor device enclosure.

37. The method according to claim 32, further comprising altering the at least one environmental parameter using a vent aperture defined in the sensor device enclosure that is configured to be operably engaged with a conduit.

38. The method according to claim 32, wherein said conveying the sensor device comprises conveying the sensor device using a linear actuator device.

39. The method according to claim 38, wherein the linear actuator device comprises a screw drive for conveying the sensor device to at least one of the measuring position and the verification position.

40. The method according to claim 38, wherein the linear actuator device comprises a plurality of adjustable stops corresponding to a plurality of discrete positions including at least one of the measuring position and the verification position, and wherein the linear actuator device responds to the adjustable stops so as to be capable of conveying the sensor device to each of the plurality of discrete positions.

41. The method according to claim 32, wherein said conveying the sensor device comprises conveying the sensor device using a rotational actuator device.

42. The method according to claim 41, further comprising selectively conveying the verification device relative to the sensor device using a second actuator device such that the sensor device is capable of measuring one or more verification parameters of the verification device.

* * * * *